(12) United States Patent
Ando

(10) Patent No.: US 6,842,245 B2
(45) Date of Patent: Jan. 11, 2005

(54) PATTERN TEST DEVICE

(75) Inventor: Akihiko Ando, Kanagawa (JP)

(73) Assignee: NEC Electronics Corporation, Kanagawa (JP)

( * ) Notice: Subject to any disclaimer, the term of this patent is extended or adjusted under 35 U.S.C. 154(b) by 37 days.

(21) Appl. No.: 10/345,194

(22) Filed: Jan. 16, 2003

(65) Prior Publication Data
US 2003/0137665 A1 Jul. 24, 2003

(30) Foreign Application Priority Data
Jan. 18, 2002 (JP) ........................................ 2002-009847

(51) Int. Cl.$^7$ .............................................. G01B 11/00
(52) U.S. Cl. .................. 356/394; 356/237.1; 356/237.5
(58) Field of Search .............................. 356/394, 237.1, 356/237.2, 237.3, 237.4, 237.5, 237.6; 250/491.1, 492.2, 572; 382/8

(56) References Cited

U.S. PATENT DOCUMENTS

| | | | | |
|---|---|---|---|---|
| 3,944,369 A | * | 3/1976 | Cuthbert et al. ............ | 356/394 |
| 4,365,163 A | * | 12/1982 | Davis et al. ............. | 250/491.1 |
| 4,559,603 A | * | 12/1985 | Yoshikawa ................... | 716/5 |
| 4,692,690 A | * | 9/1987 | Hara et al. ................. | 356/394 |
| 4,718,767 A | * | 1/1988 | Hazama ..................... | 356/389 |
| 4,791,586 A | * | 12/1988 | Maeda et al. ................. | 716/5 |
| 5,173,719 A | * | 12/1992 | Taniguchi et al. .......... | 356/394 |
| 5,235,400 A | * | 8/1993 | Terasawa et al. ........ | 356/237.5 |

FOREIGN PATENT DOCUMENTS

JP        10-38812        2/1998

* cited by examiner

Primary Examiner—Frank G. Font
Assistant Examiner—Sang H. Nguyen
(74) Attorney, Agent, or Firm—Young & Thompson

(57) ABSTRACT

A pattern test device has a reference data generator for generating reference pattern data and setting a first sub-area or a second sub-area in a mask area depending on the accuracy for the pattern test. A threshold selecting section selects first or second threshold depending on the test location residing in the first sub-area or second sub-area, whereby the judgement section judges presence or absence of a defect in the mask area while using the first or second threshold to compare therewith difference data between the test pattern data and the reference pattern data.

18 Claims, 7 Drawing Sheets

PATTERN TEST DEVICE

BACKGROUND OF THE INVENTION (a) Field of the Invention

The present invention relates to a pattern test device and, more particularly, to a pattern test device for detecting a defect in a test pattern data by comparing the test pattern data obtained by imaging a mask pattern against a reference pattern data. The present invention also relates to a pattern test method.

(b) Description of the Related Art

A typical test method for detecting a defect in a mask pattern or reticle pattern (simply referred to as mask pattern in this text) uses a test pattern data obtained by imaging the mask pattern in a mask by using a CCD camera or optical imaging system, for example. The test pattern data are compared against corresponding reference pattern data or design data stored in a CAD system for electron beam writing.

FIG. 5 shows an example of a conventional pattern test device. The pattern test device, generally designated by numeral 11, includes an imaging system 12, a conversion section 13, a comparator 15, a judgement section 16, and a review section 17 such as including a display unit.

The imaging system 12 picks-up an image from the mask pattern in a mask under test, to thereby generate test pattern data, and delivers the same to the comparator 15. The test pattern data includes a plurality of unit pixel data, which are encoded into gray-scale levels from 0 to 255 depending on the brightness thereof, for example.

The conversion section 13 receives electron beam data (EB data) stored in the CAD system corresponding to the mask pattern data, converts the EB data into reference pattern data having a data format same as the data format of the test pattern data, and delivers the converted EB data as reference pattern data to the comparator 15.

The comparator 15 compares the test pattern data delivered from the imaging system 12 against the reference pattern data delivered from the conversion section 13, to deliver differential data between the test pattern data and the reference pattern data to the judgement section 16. The term "differential data" as used herein include level difference data representing a difference between the gray-scale level of the test pattern data and the gray-scale level of the reference pattern data for each pixel, and differential difference data representing a difference between the differentiated data of the test pattern data with respect to the dimension in a specified direction and the differentiated data of the reference data with respect to the dimension in the specified direction.

The judgement section 16 stores therein threshold values used for judging as to whether or not the difference data exhibit a defect in the test pattern data. The judgement section 16 compares the difference data including the level reference data and the differential difference data against the respective threshold values, to judge presence or absence of the defect depending on the magnitude of the difference data with respect to the threshold values. The judgement section 16 stores therein the to coordinates of the defect thus judged and the image data of the vicinity of the defect. The judgement section 16 then delivers the coordinates and the image data of the defect to the review section 17.

The review section 17, or display unit, displays the image of the vicinity of the defect based on the coordinate information and the image data received from the judgement section 16. The operator observes the image on the review section 17 and determines the size and type of the defect as well as the influence thereby upon the resultant semiconductor device.

It is to be noted that different defects in the mask pattern have different influences on the resultant LSI (or semiconductor device) depending on the location of the defects in the mask pattern even if the defects have similar sizes. However, this is not noticed in the conventional technique, and a minor defect which has an insignificant influence on the resultant semiconductor device is also detected by the conventional technique. This reduces the throughput of the pattern test device and raises a turn around time for fabricating the semiconductor device.

Patent Publication JP-A-2000-146857 describes a technique for solving the above problem, wherein the threshold for detecting the defect is changed depending on the sub-areas of the mask. FIG. 6 shows the pattern test device described in the publication. The pattern test device 50 includes a host CPU 59, a storage disk 60, a design data input section 61, a data comparator 62 and an imaging system 52.

The imaging system 52 includes a light source 54, an illumination optical system 55, an X-Y table for mounting thereon a photomask under test, an image forming optical system 56, a photodetector 57 and a sensor circuit 58. The sensor circuit 58 has a function for encoding the output from the photodetector 57.

The storage disk 60 stores therein CAD data including design pattern data of the photomask 51. The host CPU 59 reads the CAD data from the storage disk 60, and the design data input section 61 receives the design pattern data in the CAD data from the host CPU 59 to deliver the same as the reference pattern data to the data comparator 62.

The imaging system 52 detects the pattern of the photomask 51 by using the function of the optical systems 55 and 56 and the photodetector 57, and delivers the test pattern data representing the imaged patterns of the photomask 51 to the data comparator 62 through the sensor circuit 58.

FIG. 7 shows the explanatory diagram for showing the principle of the pattern test device of FIG. 6, wherein the thresholds are changed for the sub-areas in the mask area 63 of the photomask 51. In the pattern test device 50, the host CPU 59 delivers, to the data comparator 62, data for dividing the mask area 63 of the photomask 51 into sub-areas A, B and C for which respective thresholds are determined beforehand.

FIG. 8 shows the functional block diagram of the data comparator 62, which includes a differential comparator block 70 and a level comparator 71. The differential comparator block 70 includes a differential circuit 77, an edge orientation detector 72, an edge differentiation circuit 73, a selector 74, a maximum detector 75 and a subtracter 76.

The differentiation circuit 77 differentiates the test pattern data with respect to the orientations of X-axis, Y-axis and orientations ±45 degrees away from the X-axis, and delivers the absolute values of the differentials to the selector 74. The edge orientation detector 72 detects the orientation of an edge of a pattern based on the design pattern data. The edge differentiation circuit 73 differentiates the pixel data with respect to the orientation of the edge of the pattern received from the edge orientation detector 72. The maximum detector 75 detects the maximum absolute value among the differentials of the pixel data around the pattern.

The selector 74 selects one of the absolute values of the differentials which is differentiated with respect to an orientation same as the orientation of the edge of the pattern detected by the edge orientation detector 72.

The subtracter 76 subtracts the maximum differential detected by the maximum detector 75 from the differential selected by the selector 74, and delivers the differential difference to the judgement section 78.

The judgement section 78 compares the differential difference delivered from the subtracter 76 against the threshold, which is predetermined for the sub-area of the mask, to thereby detects a defect. The information of the defect thus detected is delivered as defect data through an OR gate 79.

In the conventional technique described in the above publication, since the mask area must be divided into a large number of sub-areas beforehand, the division itself costs large man-hours. In addition, the judgement section 78 or 80 must determine the threshold for comparison each time the pattern test advances crossing a boundary between the sub-areas, which complicates the control for the comparator in the pattern test device and thus reduces the throughput of the pattern test device.

SUMMARY OF THE INVENTION

In view of the above problems in the conventional technique, it is an object of the present invention to provide a pattern test device which is capable of reducing man-hours for dividing the mask area into a plurality of sub-areas, and raising the throughput for judgement in the pattern test device.

It is another object of the present invention to provide a pattern test method to be used in the pattern test device of the present invention.

The present invention provides a pattern test device including: an imaging section for imaging a mask pattern in a mask area to generate test pattern data; a reference data generator for generating reference pattern data corresponding to the test pattern data based on design data from which the mask pattern is generated, the reference pattern data generator setting a first sub-area and a second sub-area in the mask area based on the design data and other design data from which at least one another mask pattern is generated; a threshold selecting section for selecting a first threshold or a second threshold for a test location in the mask area, depending on the test location residing in the first sub-area or the second sub-area; a comparator for comparing the test pattern data against the reference pattern data to generate difference data therebetween; and a judgement section for judging presence or absence of a defect at the test location by comparing the difference data against the first or second threshold selected by the threshold selecting section.

The present invention also provides a pattern test method including the steps of; imaging a mask pattern in a mask area to generate test pattern data; etting a first sub-area and a second sub-area in the mask area based on the design data and other design data from which at least one another mask pattern is generated; selecting a first threshold or a second threshold for a test location in the mask area, depending on the test location residing in the first sub-area or the second sub-area; comparing the test pattern data against reference pattern data to generate difference data therebetween; and judging presence or absence of a defect at the test location by comparing the difference data against the first or second threshold selected in the threshold selecting step.

In accordance with the pattern test device and the pattern test method of the present invention, since the first and the second sub-areas are set based on the mask pattern data (or reference data) and another mask pattern data, the setting of the sub-areas is conducted without man-hours and thus raises the throughput of the pattern test process.

The above and other objects, features and advantages of the present invention will be more apparent from the following description, referring to the accompanying drawings.

PREFERRED EMBODIMENTS OF THE INVENTION

Now, the present invention is more specifically described with reference to accompanying drawings.

Figure 1:
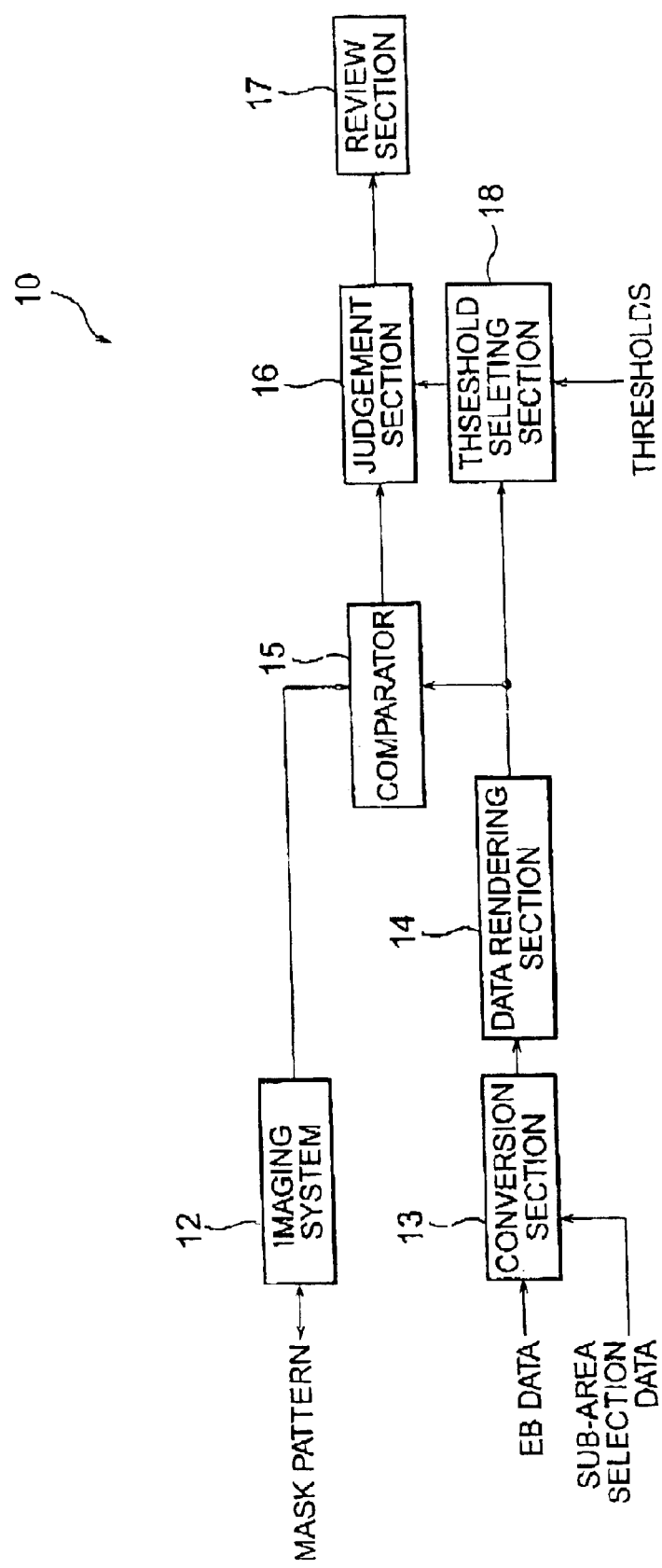
FIG. 1 is a block diagram of a pattern test device according to a first embodiment of the present invention.

Referring to FIG. 1, a pattern test device, generally designated by numeral 10, according to a first embodiment of the present invention includes an imaging system 12, a conversion section (reference pattern generator) 13, a data rendering section 14, a comparator 15, a judgement section 16, a review section 17 and a threshold selecting section 18.

The imaging system 12 picks-up the image of a mask pattern (or reticle pattern) to generate test pattern data, and delivers the same to the comparator 15. The test pattern data includes a plurality of unit pixel data, each of which is encoded to have a gray scale level from 0 to 255 depending on the brightness, or gray scale level, of the unit pixel.

Figure 4:
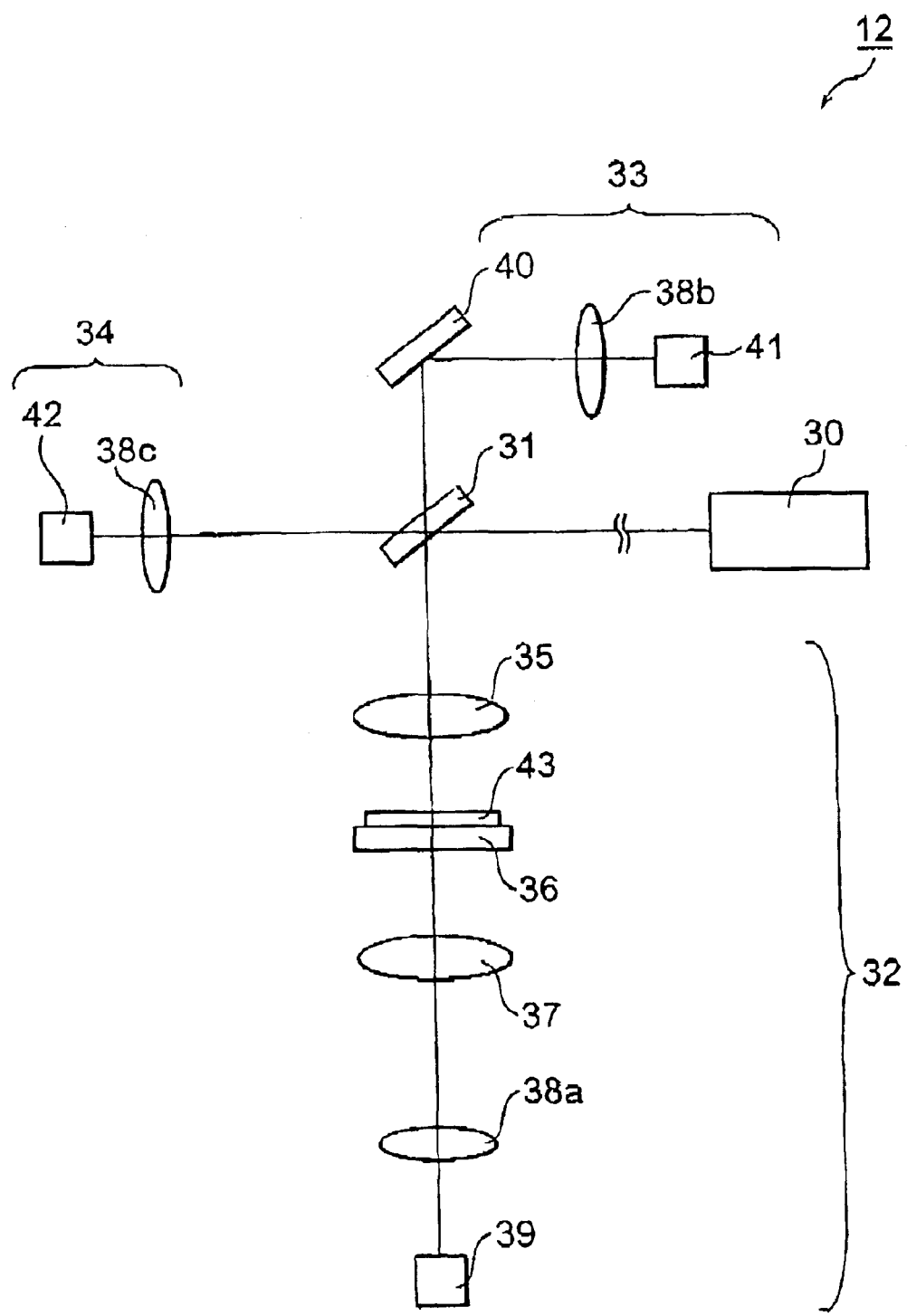
FIG. 4 is a schematic block diagram of the imaging system shown in FIG. 1.
Figure 5:
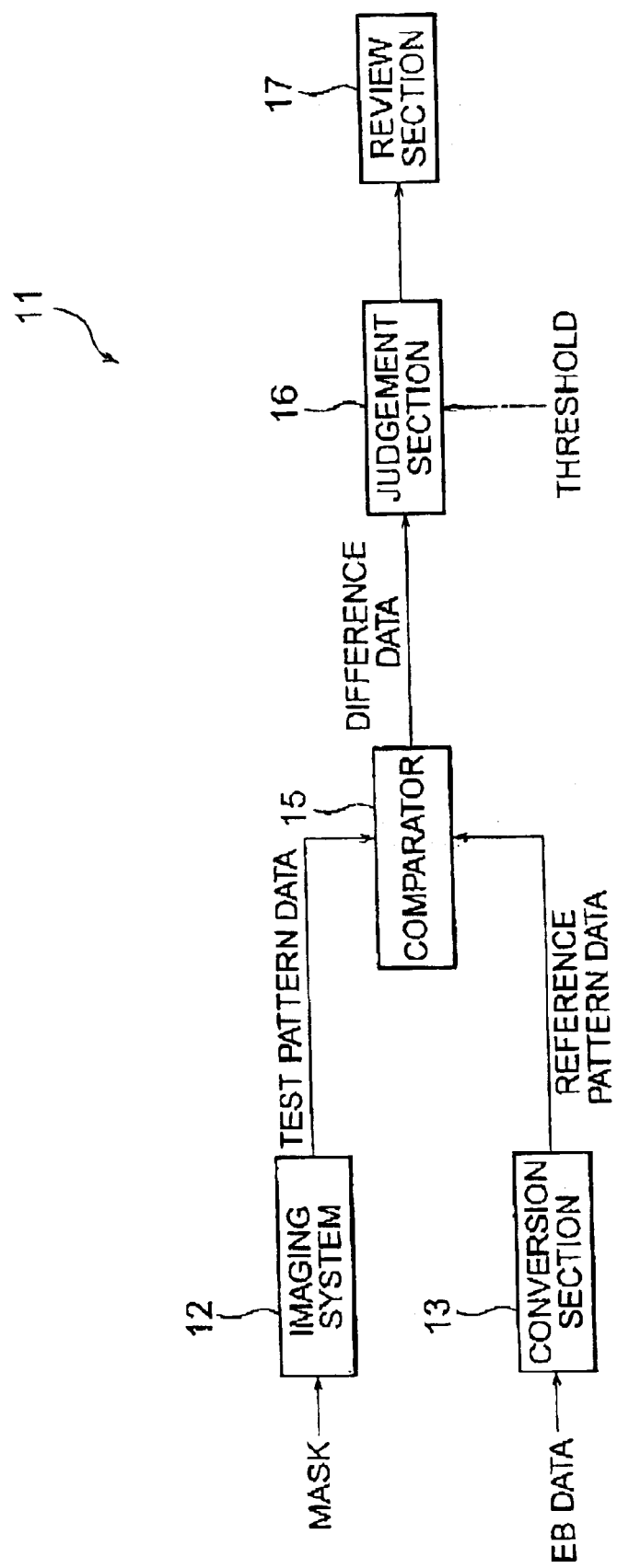
FIG. 5 is a block diagram of a conventional pattern test device.
Figure 6:
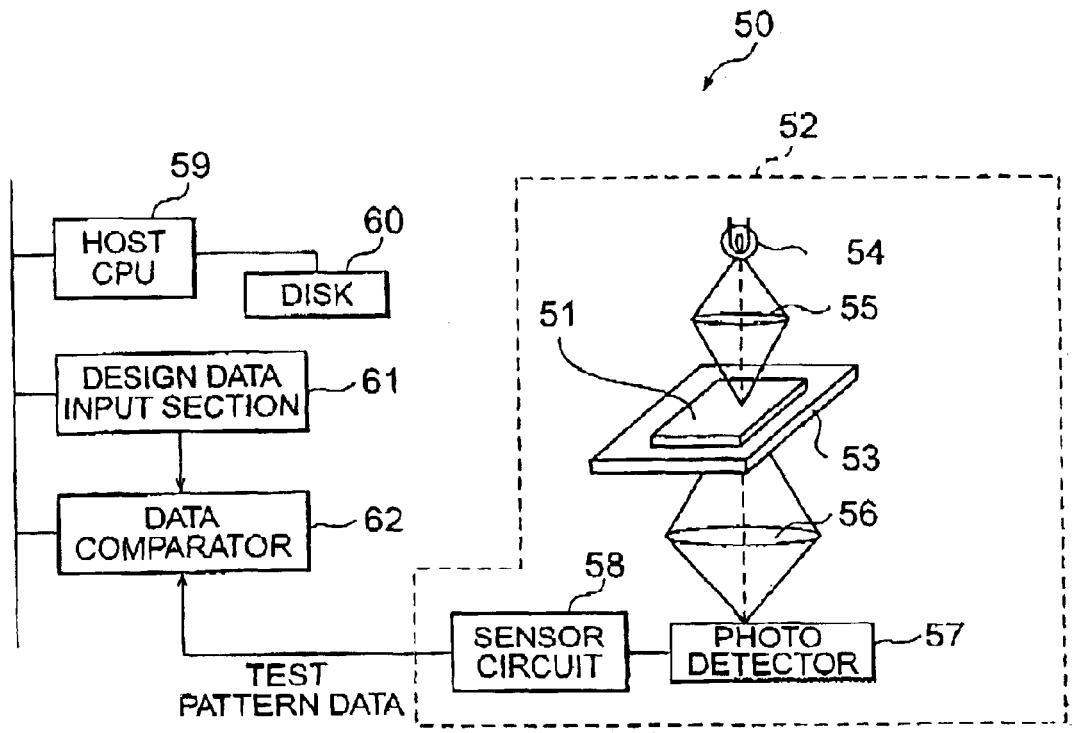
FIG. 6 is a block diagram of the pattern test device described in a patent publication.
Figure 7:
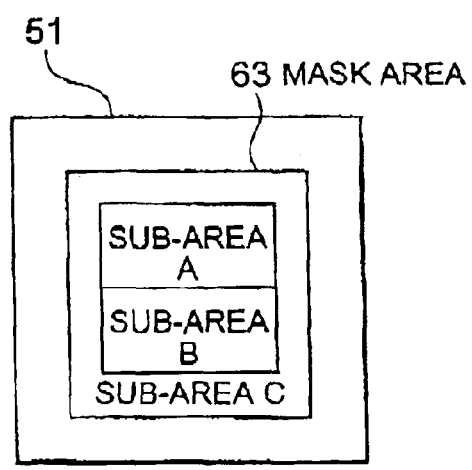
FIG. 7 is an explanatory top plan view of a mask to be tested by the pattern test device of FIG. 6.
Figure 8:
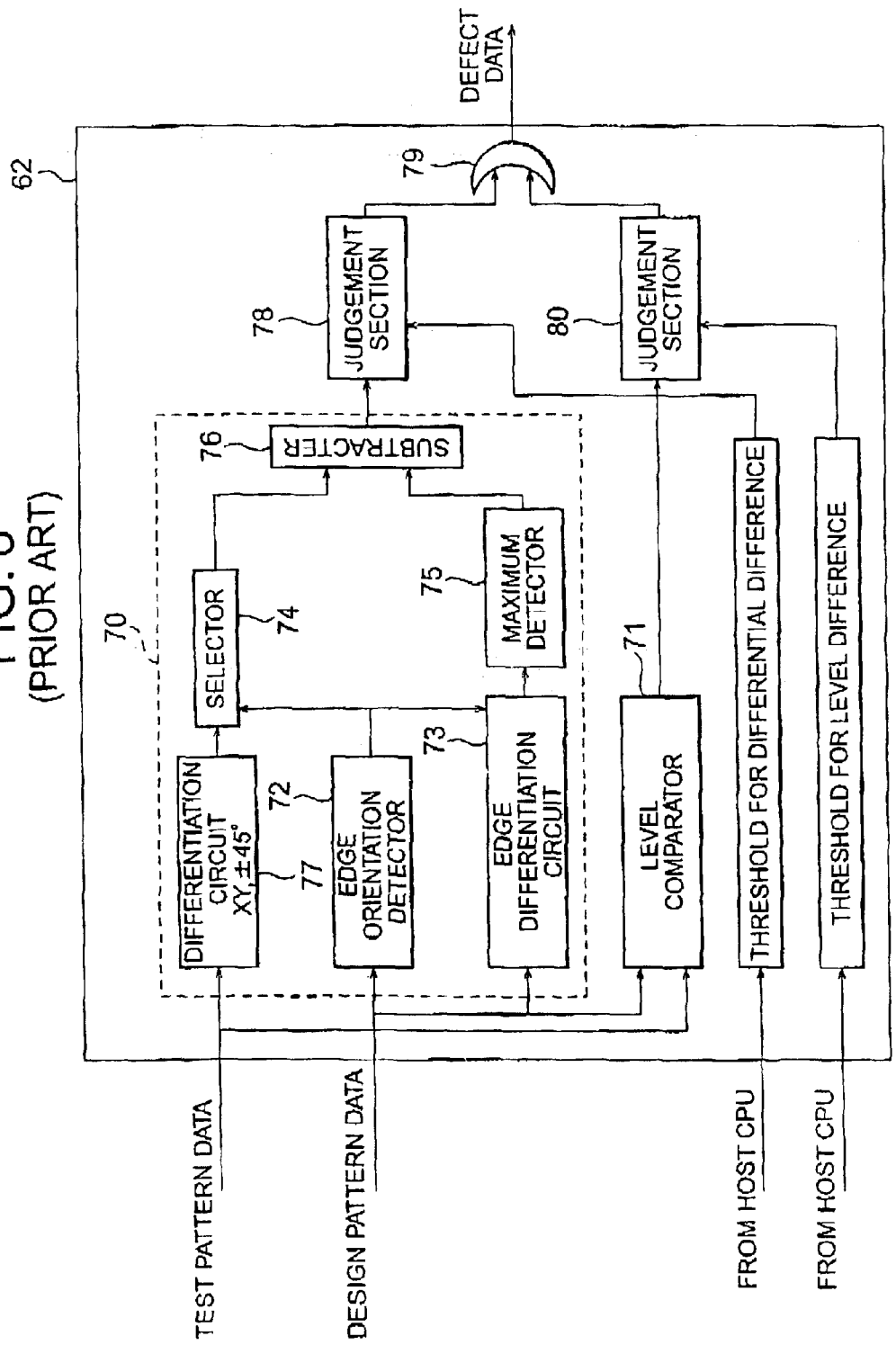
FIG. 8 is a block diagram of the data comparator shown in FIG. 6.

Referring to FIG. 4, the imaging system 12 includes a laser device 30, a half mirror 31, a transmission-beam optical system 32, a reflection-beam optical system 33 and a monitor optical system 34. The imaging system 12 picks-up the image of the mask 43 under test by taking advantage of the dispersion of laser.

The laser device 30 is an argon (Ar) laser, for example. The transmission-beam optical system 32 includes an objective lens 35, an X-Y stage 36 mounting thereon the mask 43, a contact lens 37, a condenser lens 38a, and a first photodetector 39. The reflection-beam optical system 33 includes a reflector 40, a condenser lens 38b, and a second photodetector 41. The monitor optical system 34 includes a condenser lens 38c and a monitor photodetector 42.

The optical beam emitted from the laser device 30 is partly reflected by the half mirror 31 toward the transmission-beam optical system 32, reduced in the diameter thereof by the objective lens 35, and irradiated onto the mask 43. Most of the optical beam passed by the mask 43 advances through the contact lens 37 and the condenser lens 38a to be received by the first photodetector 39 for measurement of the optical amount thereof.

The remaining optical beam reflected by the mask 43 advances through the objective lens 35 and the half mirror 31 toward the reflection-beam optical system 33, is reflected by the mirror 40 disposed above the half mirror 31, and advances through the condenser lens 38b to be received by the second photodetector 41 for measurement of the optical amount thereof.

Some of the optical beam emitted from the laser device 30 and passed by the half mirror 31 advances through the condenser lens 38c to be received by the monitor photodetector 42 for measurement of the optical amount thereof.

The optical beam incident onto the mask pattern 34 is a spotlight, which is scanned on the mask pattern 34 to detect a defect on the mask pattern 34. The scan technique for the spotlight may be a ladder scan wherein the optical beam is scanned in the Y-direction by the half mirror 31 while the X-Y stage 36 is moved in the X-direction.

The intensity of the optical beam at each position of the mask pattern 34 and measured by the first photodetector 39 is normalized by the intensity of the optical beam measured by the monitor photodetector 42 for each pixel, and encoded into a gray-scale level. The intensity of the optical amount measured by the second photodetector 41 is also normalized and encoded similarly, and may be used as a reference for the pattern test on the screen of the review section 17.

The conversion section 13 shown in FIG. 1 receives EB data (or subject mask data) corresponding to the test pattern data and other mask data, as sub-area selection data, which is to be overlapped with the EB data in an LSI. The conversion section 13 converts these data into reference pattern data having a data format corresponding to the data format of the test pattern data and specified sub-area data having information of specified sub-areas. Subsequently, the conversion section 13 delivers the reference data and the specified sub-area data to the data rendering section 14.

Figure 2C:
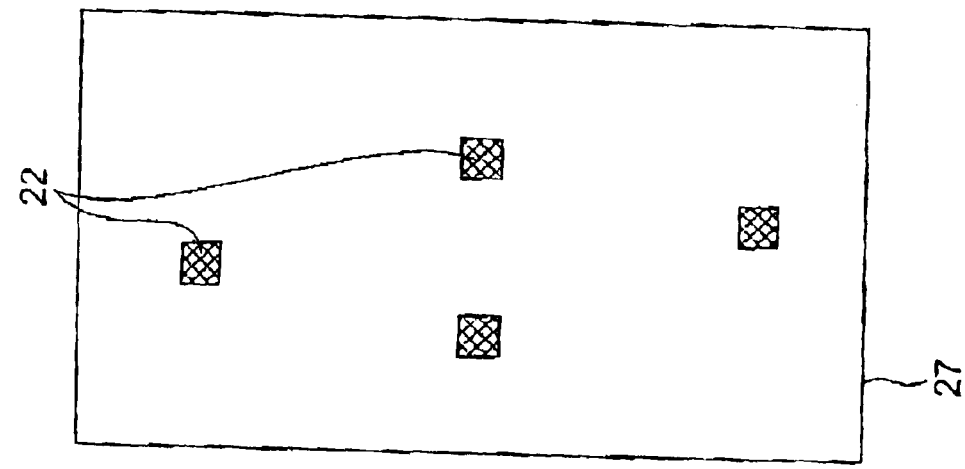
FIGS. 2A to 2C are top plan views of mask patterns to be tested by the pattern test device of FIG. 1.
Figure 2B:
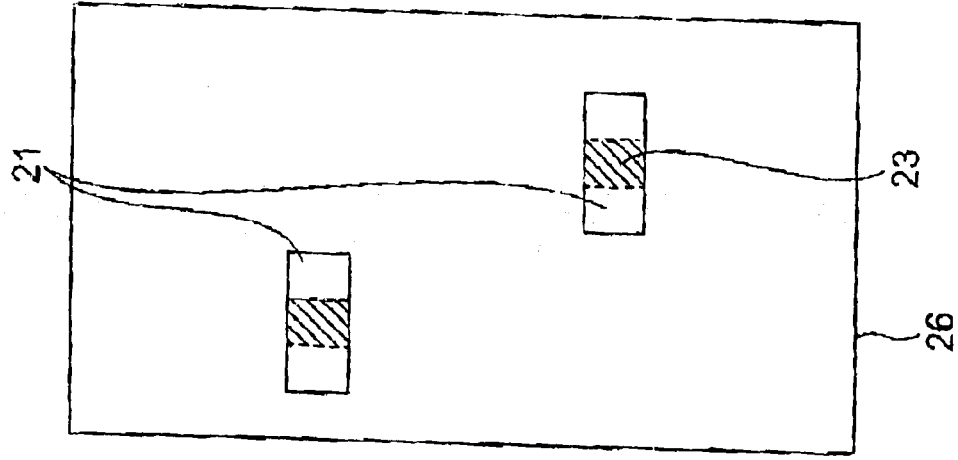
Figure 2A:
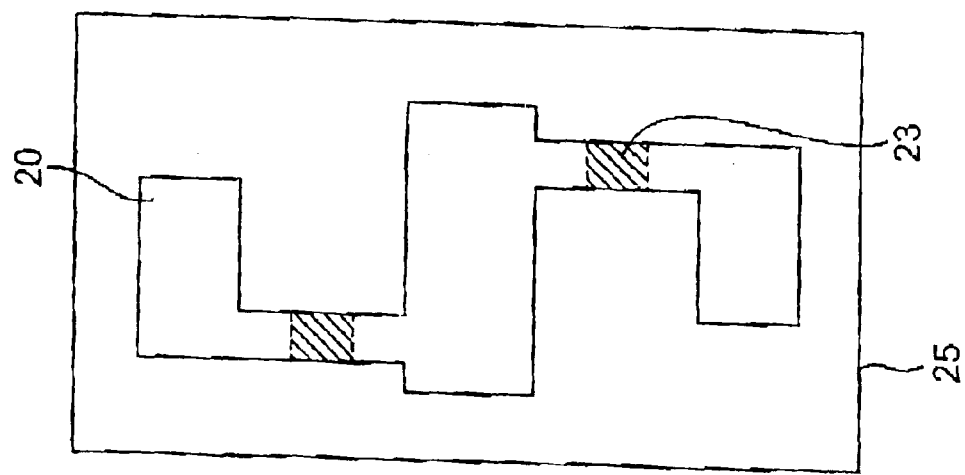

An example for generating the specified sub-area data is now described with reference to FIGS. 2A to 2C and FIGS. 3A and 3B. FIG. 2A shows the mask area 25 of a mask used for forming a gate-electrode pattern, FIG. 2B shows the mask area 26 of a mask used for forming a field-area pattern, and FIG. 2C shows the mask area 27 of a mask used for forming a contact-area pattern in an LSI. The field area 21 is such that exposed from a field oxide film, or LOCOS film, formed on a semiconductor substrate and underlies the gate electrode 20 in an LSI. The contact area 22 is used for connecting the gate electrode 20 with an overlying metallic line. The LSI is generally obtained after a plurality of photolithographic etching steps are conducted using these masks.

In the example shown in FIGS. 2A to 2C, it is determined that the specified sub-areas which require more accurate patterning are diffused regions denoted by numeral 23 and the vicinity thereof. The diffused regions 23 can be expressed by the overlapping portion between the gate electrode 20 shown in FIG. 2A and the field area 21 shown in FIG. 2B. Thus, by overlapping the mask pattern of the gate electrode 20 and the mask pattern of the field area 21, the diffused regions 23 and the vicinities thereof are obtained.

Figure 3B:
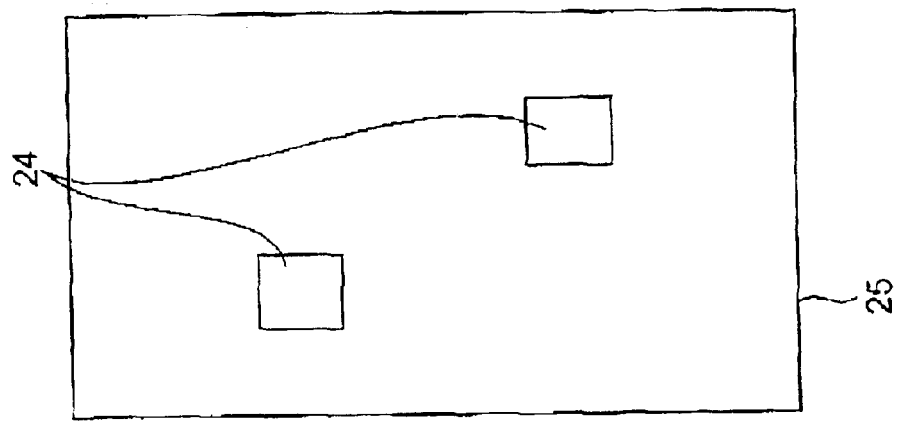
FIGS. 3A and 3B are explanatory top plan views for showing establishment of selected sub-areas in the mask area by the pattern test device of FIG. 1.
Figure 3A:
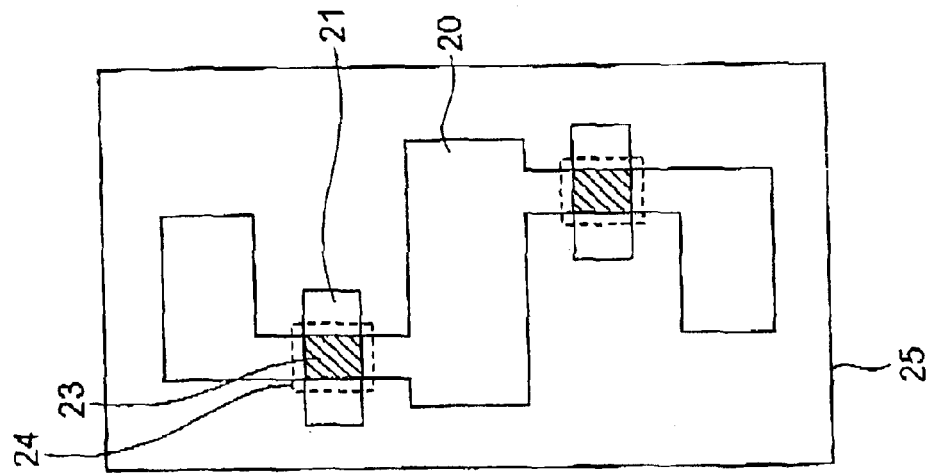

FIG. 3A shows the situation for determining the specified sub-areas 24 by using the masks for the gate electrode 20 and the field area 21. FIG. 3B shows the specified sub-areas 24 determined by the above procedure. The specified sub-area 24 includes the overlapping portion (23 shown in FIG. 3A) between the mask patterns and the vicinity thereof. The range of the vicinity should be determined for assuring absence of the defect in the mask pattern by considering the relationship between the elements formed by these patterns. The data including information of the specified sub-areas 24 and the non-specified sub-area is called herein specified sub-area data.

Back to FIG. 1, the data rendering section 14 receives the reference pattern data and the specified sub-area data from the conversion section 13, temporarily stores these data and delivers these data to the comparator 15 pixel by pixel while monitoring the test location at which the imaging system 12 picks-up the image of the mask.

The comparator 15 compares the test pattern data delivered from the imaging system 12 against the reference data delivered from the data rendering section 14, to detect the difference data therebetween, which is delivered to the judgement section 16.

The "difference data" include level difference data, differential difference data, and/or the edge error data in the mask pattern. The level difference data is obtained by comparing the gray-scale level of the pixel against the corresponding reference data. The differential difference data is obtained by comparing the differential data of the gray-scale level of the pixel against the corresponding data obtained from the reference data. The edge error data is obtained by comparing the location at which the gray-scale level most changes between pixels against the corresponding locational data obtained from the reference data. The differential data include such obtained by differentiating the gray-scale levels of pixels with respect to X-axis, Y-axis and directions ±45 degrees away from X-axis.

In the threshold selecting section 18, threshold values are stored beforehand for respective sub-areas, or specified sub-areas and non-specified sub-areas, for the judgement in the judgement section 16, depending on the accuracy with which the pattern test should be conducted. The threshold selecting section 18 selects one of the threshold values for the test location based on the test location supplied through the data rendering section 14 while using a specified algorithm for the selection.

The judgement section 16 receives the difference data from the comparator 15, receives the threshold value corresponding to the sub-area of the pixel from the threshold selecting section 18, compares the difference data against the received threshold value, and detects the presence or absence of a defect. If a defect is detected, the judgement section 16 stores therein the locational information, or coordinates, of the defect and the image of the vicinity thereof. The judgement section 16 then delivers the locational information and the image data to the review section 17.

The review section 17 includes a screen which displays thereon the image of the defect, based on which the operator confirms that the detected defect is critical for the LSI and judges the type of the defect or the influence upon the resultant LSI.

In the above embodiment, the specified sub-areas can be determined based on the overlapping portions between the patterns of a plurality of masks without any manual procedure, which raises the throughput of the determination of the sub-areas and comparison of the test pattern data against the reference data.

A plurality of specified sub-areas having respective threshold values may be determined based on different combinations of the mask patterns.

Since the above embodiments are described only for examples, the present invention is not limited to the above embodiments and various modifications or alterations can be easily made therefrom by those skilled in the art without departing from the scope of the present invention.

What is claimed is:

1. A pattern test device comprising:

an imaging section for imaging a first mask pattern in a mask area to generate test pattern data and for imaging a second mask pattern in the mask area to generate further test pattern data;

a reference data generator for generating reference pattern data corresponding to said test pattern data based on design data from which said first mask pattern is generated, said reference pattern data generator setting a first sub-area and a second sub-area in said mask area based on said test pattern data and said further test pattern data;

a threshold selecting section for selecting a first threshold or a second threshold for a test location in said mask area, depending on said test location residing in said first sub-area or said second sub-area;

a comparator for comparing said test pattern data against said reference pattern data to generate difference data therebetween; and a judgment section for judging presence or absence of a defect at said test location by comparing said difference data against said first or second threshold selected by said threshold selecting section.

2. The pattern test device according to claim 1, wherein said first mask pattern and said further mask pattern are overlapped with one another on an LSI.

3. The pattern test device according to claim 2, wherein said reference data generator sets, as said first sub-area, an overlapping portion between said first mask pattern and said second mask pattern and a vicinity of said overlapping portion.

4. The pattern test device according to claim 1, wherein said mask pattern is a reticle pattern for manufacturing a mask.

5. The pattern test device according to claim 1, said mask pattern is a reticle pattern for manufacturing a mask.

6. A pattern test method comprising the steps of:

imaging a first mask pattern in a mask area to generate test pattern data;

imaging a second mask pattern in the mask area to generate further test pattern data;

setting a first sub-area and a second sub-area in said mask area based on said test pattern data and said further test pattern data;

selecting a first threshold or a second threshold for a test location in said mask area, depending on said test location residing in said first sub-area or said second sub-area;

comparing said test pattern data against reference pattern data to generate difference data therebetween; and judging presence or absence of a defect at said test location by comparing said difference data against said first or second threshold selected in said threshold selecting step.

7. The pattern test method according to claim 6, wherein said first mask pattern and said second mask pattern are overlapped with one another on an LSI.

8. The pattern test method according to claim 6, wherein said setting step sets, as said first sub-area, an overlapping portion between said first mask pattern and said second mask pattern and a vicinity of said overlapping portion.

9. A pattern test device comprising:

an imaging section for imaging a mask pattern to generate test pattern data including a plurality of pixel data;

a reference data generator for converting design data of said mask pattern into a first reference pattern data including a plurality of pixel data, converting design data of another mask pattern into a second reference pattern data including a plurality of pixel data, said mask pattern and said another mask pattern being used for exposure on a wafer, and setting a first area on an overlapping data area in which said first reference pattern data overlaps with said second reference pattern data and a second area other than said first area;

a comparator for comparing said test pattern data against said first reference pattern data to generate difference data therebetween; and a judgment section for judging presence or absence of a defect by comparing said difference data against a first threshold in said first area and comparing said difference data against a second threshold in said second area.

10. The pattern test device according to claim 9, wherein each of said pixel data has a gray scale level based on a brightness of a corresponding pixel.

11. The pattern test device according to claim 10, wherein said difference data includes a difference between gray scale levels.

12. The pattern test device according to claim 10, wherein said difference data includes a difference between differentials of gray scale levels.

13. The pattern test device according to claim 9, wherein said first area includes a vicinity of said overlapping data area.

14. A pattern test method comprising the steps of:

imaging a mask pattern to generate test pattern data including a plurality of pixel data;

converting design data of said mask pattern into a first reference pattern data including a plurality of pixel data;

converting design data of another mask pattern into a second reference pattern data including a plurality of pixel data, said mask pattern and said another mask pattern being used for exposure on a wafer;

setting a first area on an overlapping data area in which said first reference pattern data overlaps with said second reference pattern data and a second area other than said first area;

comparing said test pattern data against said first reference pattern data to generate difference data therebetween; and judging presence or absence of a defect by comparing said difference data against a first threshold in said first area and comparing said difference data against a second threshold in said second area.

15. The pattern test method according to claim 14, wherein each of said pixel data has a gray scale level based on a brightness of a corresponding pixel.

16. The pattern test method according to claim 15, wherein said difference data includes a difference between gray scale levels.

17. The pattern test method according to claim 15, wherein said difference data includes a difference between differentials of gray scale levels.

18. The pattern test method according to claim 14, wherein said first area includes a vicinity of said overlapping data area.

* * * * *